United States Patent
Van Deynse et al.

(10) Patent No.: US 9,006,497 B2
(45) Date of Patent: Apr. 14, 2015

(54) METHOD FOR HYDROLYZING ALPHA-CHLORINATED TOLUENE COMPOUNDS

(75) Inventors: Dirk Van Deynse, Koersel (BE); Koen Van Aken, Kuurne (BE); Wouter Van Hecke, Overmere (BE)

(73) Assignee: INEOS Chlorotoluenes Limited, Cheshire (GB)

( * ) Notice: Subject to any disclaimer, the term of this patent is extended or adjusted under 35 U.S.C. 154(b) by 0 days.

(21) Appl. No.: 14/234,595

(22) PCT Filed: Jul. 26, 2011

(86) PCT No.: PCT/EP2011/062850
§ 371 (c)(1),
(2), (4) Date: Jan. 23, 2014

(87) PCT Pub. No.: WO2013/013709
PCT Pub. Date: Jan. 31, 2013

(65) Prior Publication Data
US 2014/0155657 A1    Jun. 5, 2014

(51) Int. Cl.
*C07C 37/02* (2006.01)
*C07C 29/124* (2006.01)

(52) U.S. Cl.
CPC ............... *C07C 37/02* (2013.01); *C07C 29/124* (2013.01)

(58) Field of Classification Search
USPC .......................................... 568/796, 797, 777
See application file for complete search history.

(56) References Cited

U.S. PATENT DOCUMENTS

| 3,562,321 A | 2/1971 | Borkowski et al. |
| 4,474,993 A | 10/1984 | Hag et al. |
| 5,728,897 A | 3/1998 | Buysch et al. |
| 8,614,173 B2 * | 12/2013 | Tanabe .......................... 508/165 |

FOREIGN PATENT DOCUMENTS

| GB | 1303376 A | 1/1973 |
| JP | 48-5733 | 2/1973 |

OTHER PUBLICATIONS

International Search Report and Written Opinion of the International Searching Authority for International Application No. PCT/EP2011/062850, mailed on Apr. 26, 2012.

* cited by examiner

*Primary Examiner* — Sudhakar Katakam
*Assistant Examiner* — Pancham Bakshi
(74) *Attorney, Agent, or Firm* — Knobbe, Martens, Olson & Bear LLP

(57) ABSTRACT

The current invention provides and improved method for hydrolyzing alpha-chlorinated toluene compounds comprising the steps of:—providing an alpha-chlorinated toluene compound of formula (I) wherein at least one of $R_1$, $R_2$ and $R_3$ is Cl and wherein $(R_a)_n$ designates that the benzene nucleus may have one or more substituents which may be same or different and are selected from the group consisting of H, Cl, Br and —$C_mH_{2m+1}$, n being 0 or an integer from 1 to 5, and m being an integer, preferably from 1 to 6,—hydrolyzing said compound with water in the presence of a metal oxide.

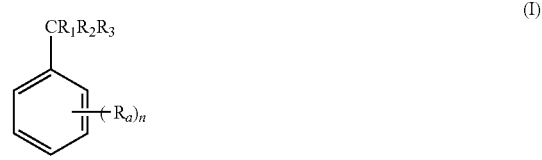

(I)

12 Claims, 3 Drawing Sheets

METHOD FOR HYDROLYZING ALPHA-CHLORINATED TOLUENE COMPOUNDS

CROSS-REFERENCE TO RELATED APPLICATIONS

This application is the U.S. National Phase under 35 U.S.C. §371 of International Application PCT/EP2011/062850, filed Jul. 26, 2011.

TECHNICAL FIELD

The invention pertains to a novel method for the hydrolysis of alpha-chlorinated toluene compounds. The method is characterized by the use of metal oxides. The method is particularly useful in the field of chemical synthesis, particularly for the production of benzyl alcohol.

BACKGROUND

The hydrolysis of alpha-chlorinated toluene compounds, in particular the hydrolysis of benzyl chloride to benzyl alcohol, is well-known.

In U.S. Pat. No. 4,474,993 a continuous method for the hydrolysis of benzyl chloride to benzyl alcohol is described, whereby the hydrolysis is accelerated in the presence of basic compounds, in particular sodium hydroxide or sodium carbonate. The hydrolysis takes place in countercurrent mode between the aqueous phase containing the hydrolyzing agent and the organic phase containing the benzyl chloride and an inert organic solvent such as toluene. After the hydrolysis, the organic phase is washed with water in a washing zone and the water is extracted with inert solvent in an extraction zone. The resulting product of the hydrolysis is thereafter separated from the organic phase by distillation, by means of two distillation columns connected in series. This method has the disadvantage that an organic solvent is required to extract the hydrolyzed product. Moreover the distillation of the inert solvent is energy consuming. Another disadvantage of the above described alkaline hydrolysis, are the stoichiometric formation of sodium chloride waste liquors that need to be disposed of.

A further problem is the formation of the undesired by-product dibenzyl ether, also known as dibenzyl oxide. The extent of dibenzyl ether formation may vary from about 0.5 to 30% by weight of the final product and is affected by a number of factors such as choice of hydrolyzing agent, temperature, concentration of hydrolyzing agent, and use of inert solvent. Thus, for instance, the use of sodium carbonate as hydrolyzing agent will give rise to a lower relative rate of formation of dibenzyl ether as compared with sodium hydroxide. Furthermore, a higher concentration of hydrolyzing agent generally gives rise to a higher relative rate of formation of dibenzyl ether. The addition of inert solvent, such as toluene, to the benzyl chloride entails a substantial reduction in the formation of dibenzyl ether. Further, a raised hydrolysis temperature will increase the production of dibenzyl ether. Today, environmental and health concerns warrant the use of processes that are more environmentally and toxicologically friendly.

In U.S. Pat. No. 5,728,897 a method is described wherein a mixture of benzyl chloride and water (10-70 mole equivalents) at 80-180° C. is used without adding alkali carbonates or organic solvents with intensive mixing under incomplete conversion. The hydrochloric acid containing aqueous stream can be concentrated with HCl from the photochlorination unit (for toluene chlorination) or converted back into chlorine by hydrochloric acid electrolysis.

Unfortunately the process of U.S. Pat. No. 5,728,897 is characterized by a lower conversion to benzyl and higher byproduct formation compared to the alkaline hydrolysis under otherwise similar conditions (i.e. water to benzyl chloride mole ratio and temperature). As the molar ratio of water to benzyl chloride decreases, the hydrochloric acid concentration and hence its activity increases by a large factor leading to significant amounts of by-products and lower conversion rates. In addition, it is observed that the benzyl alcohol concentration has an optimum during the time course of the conversion. Thereafter the generated benzyl alcohol is mainly involved in byproduct formation.

There remains a need in the art for improved methods for the hydrolysis of alpha-chlorinated toluene compounds, in particular for the manufacturing of benzyl alcohol.

The present invention aims to resolve at least some of the problems mentioned above.

The invention thereto aims to provide an improved process characterized by a high conversion rate, high yield, low by-product formation, which is economically feasible and has an interesting environmental and toxicological profile.

SUMMARY OF THE INVENTION

The invention thereto provides an improved hydrolysis process characterized in that the hydrolysis is carried out in the presence of metal oxides.

In particular, the present invention provides a method for hydrolyzing alpha-chlorinated toluene compounds comprising the steps of: providing an alpha-chlorinated toluene compound of formula (I) wherein at least one of $R_1$, $R_2$ and $R_3$ is Cl and wherein $(R_a)_n$ designates that the benzene nucleus may have one or more substituents which may be same or different and are selected from the group consisting of H, Cl, Br and —$C_mH_{2m+1}$, n being 0 or an integer from 1 to 5, and m being an integer, preferably from 1 to 6, and hydrolyzing said compound with water in the presence of a metal oxide.

In a preferred embodiment, the metal oxide is selected from the list of iron oxides, cupper oxides, aluminum oxides or mixtures thereof. In a preferred embodiment, the metal oxide is FeO, $Fe_2O_3$, $Fe_3O_4$ or mixtures thereof. In a preferred embodiment, the metal oxide is iron oxide, known as FeO.

In a preferred embodiment, the molar ratio of metal oxide to alpha-chlorinated toluene compound is from 0.5 to 1.5.

In a preferred embodiment, the molar ratio of alpha-chlorinated toluene compounds to water is from 1/10 to 1/50.

In a preferred embodiment, the alpha-chlorinated toluene compound is benzyl chloride. In a preferred embodiment, the resulting product of hydrolysis is benzyl alcohol.

In a preferred embodiment, the hydrolysis is carried out at a temperature in the range of 70° C. to 180° C.

In a preferred embodiment, the hydrolysis is carried out at a pressure in the range of 1 to 10 bars.

In a preferred embodiment, an aqueous metal chloride side stream is separated from the hydrolyzed compound.

In a preferred embodiment, chlorine gas is added to the aqueous metal chloride side stream to provide aqueous $FeCl_3$.

In a preferred embodiment of a method according to the invention, the aqueous $FeCl_3$ is transferred to a storage unit for use in water treatment.

In a preferred embodiment of the invention, the method is carried out without the addition of a water-soluble organic solvent for the extraction of the hydrolyzed compound.

In a preferred embodiment, the method is characterized by a conversion of alpha-chlorinated toluene compound of at least 85%.

A process according to an embodiment of the invention is applicable at an industrial scale, is economically feasible, provides a side stream product which can be valorized and for which there is a high demand. Improved yields and conversions can be obtained. The process uses materials which are easily available. Use of an organic solvent as extraction means is avoided. Therefore a process according to an embodiment of the invention is more sustainable.

DESCRIPTION OF FIGURES

The lines in FIGS. 2 and 3 represent the reaction products in the hydrolysis reaction without iron oxide. In FIG. 2, the uninterrupted line represents benzyl alcohol, the dashed line represents benzyl chloride and the line formed with stripes and dots represents dibenzyl oxide. In FIG. 3, the full line which at t=0 at 1, represents benzyl chloride. The full line which at t=0 is at 0 and rises to nearly 0.7 represents benzyl alcohol. The third full line, at 0 at t=0 and remaining below 0.2 during the reaction, represents dibenzyl oxide.

Figure 2:
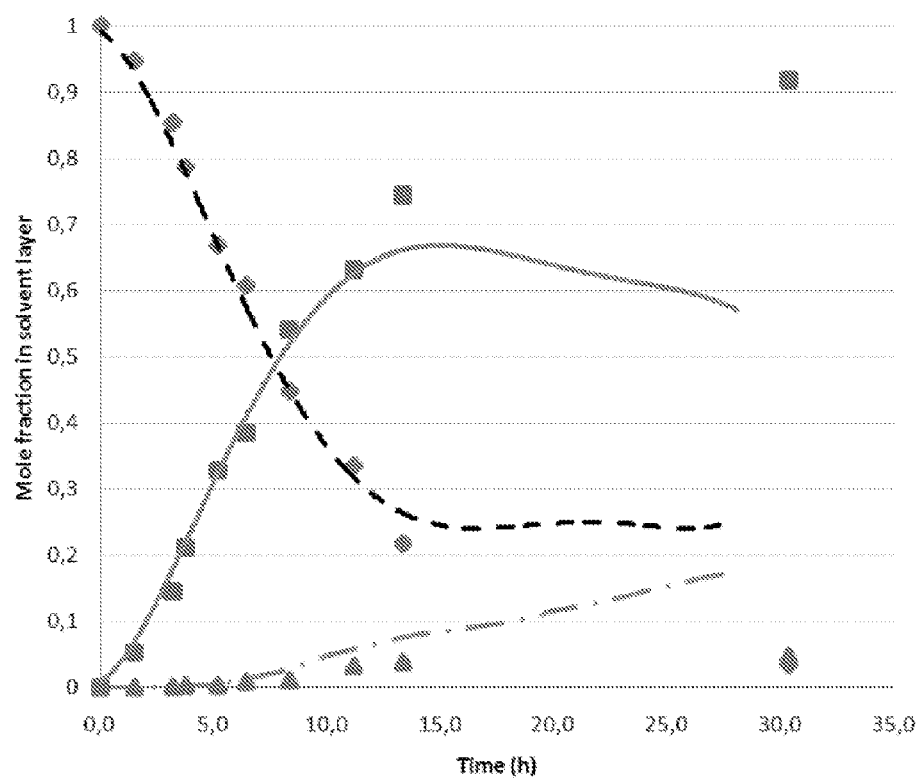
FIG. 2 is a graphic presentation of the time course of an hydrolysis reaction, with and without FeO as hydrolysing agent. The metal oxide used was FeO. Conditions: T=100° C., the weight ratio of benzyl chloride to water was 1/3.
Figure 3:
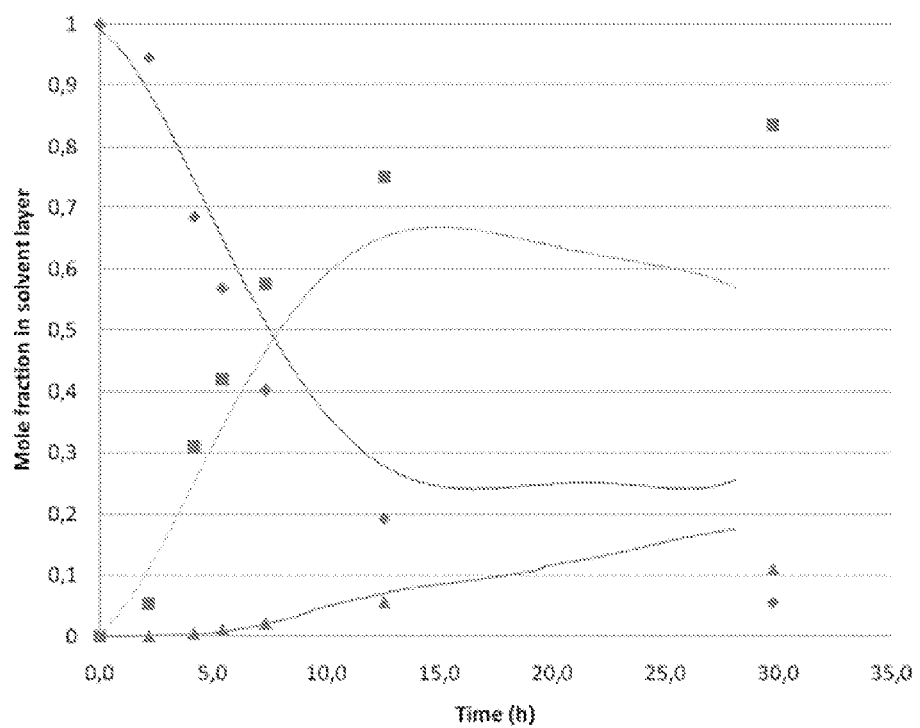
FIG. 3 is a graphic presentation of the time course of a hydrolysis reaction, with and without $Fe_2O_3$ as hydrolysing agent.

The symbols in FIGS. 2 and 3 represent data points of the hydrolysis reaction with iron oxide (FIG. 2) or Fe2O3 (FIG. 3) respectively. The squares represent the formation of benzyl alcohol. The diamonds represent benzyl chloride disappearance and the triangles represent dibenzyl oxide by-product.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The present invention concerns the hydrolysis of alpha-chlorinated toluene compounds in the presence of metal oxides. The use of toluene compounds with a chlorinated substituent is advantageous as it provides a leaving group which is easily removable.

By the term "alpha-chlorinated toluene compounds" as used herein, it is meant alpha-chlorinated toluenes and toluene derivatives of the formula (I), wherein at least one of $R_1$, $R_2$ and $R_3$ is Cl; preferably a single group is Cl;

and wherein $(R_a)_n$ designates that the benzene nucleus may have one or more substituents which may be same or different and are selected from the group consisting of H, Cl, Br and —$C_mH_{2m+1}$, n being 0 or an integer from 1 to 5, and m being an integer, preferably from 1 to 6. Preferably the alpha chlorinated toluene compounds are selected from benzyl chloride, $C_6H_5CH_2Cl$, or benzal chloride, $C_6H_5CHCl_2$, which by hydrolysis are converted to benzyl alcohol, $C_6H_5CH_2OH$, and benzaldehyde, $C_6H_5CHO$, respectively.

The most preferred embodiment of the invention relates to the hydrolysis of benzyl chloride to benzyl alcohol. At room temperature, benzyl alcohol is a colorless liquid having a density of 1.042-1.047 g/cm3 and a boiling point of 206° C. In alcohol and ether, benzyl alcohol is readily soluble, whereas in water it is only soluble in the proportion of 4/100 at 25° C. Benzyl alcohol has a wide range of applications. It is used for instance within the photographic industry, the cosmetic industry, the pharmaceutical industry, the textile industry and the dye and lacquer industry.

Several metals in oxide form are suitable for use in the invention. Preferably the metal oxide is an iron oxide, copper oxide, aluminum oxide or mixtures thereof.

Different metal valencies are suitable. In case of iron oxides, iron (II) oxide (FeO), iron (III) oxide and mixtures thereof are suitable. The iron metal in this oxide has a valency of respectively II or III.

FeO, also known as ferrous oxide or Iron (II) oxide, occurs in nature as the mineral wüstite. Preparation methods are known to a person skilled in the art. For instance, by heating iron(II) oxalate in vacuum:

$FeC_2O_4 \rightarrow FeO+CO+CO_2$

Fe2O3, also known as ferric oxide or iron (III) oxide, occurs in nature as the mineral hematite. Iron (III) oxide occurs in different forms: alpha phase, beta phase, gamma phase or epsilon phase. The most common form is alpha-Fe2O3, which has a rhombohedral structure. Preparation methods are known to a person skilled in the art. It can for instance be prepared on a laboratory scale by electrolyzing a solution of sodium bicarbonate in the presence of an inert electrolyte and an iron anode. At about 200° C. the iron (III) hydroxide converts into $Fe_2O_3$:

$$4Fe+3O_2+2H_2O \rightarrow 4FeO(OH)$$

$$2FeO(OH) \rightarrow Fe_2O_3+H_2O$$

$Fe_3O_4$ is found in nature as the mineral magnetite. It contains both Fe2+ and Fe3+ ions. It is also known under the formulation $FeO \cdot Fe_2O_3$. It is commercially available as a black powder. Most preferably it is synthesized rather than being extracted from the naturally occurring mineral as the particle size and shape can be varied by the method of production. $Fe_3O_4$ can be synthesized by methods known to a person skilled in the art. Suitable methods include:

the oxidation of iron metal in the Laux process starting from nitrobenzene which is reacted with iron meal using $FeCl_2$ as a catalyst to produce aniline;

$$C_6H_5NO_2+9Fe+2H_2O \rightarrow C_6H_5NH_2+Fe_3O_4$$

the oxidation of Fe(II) compounds, such as the precipitation of iron(II) salts as hydroxides followed by oxidation by aeration where control of the pH determines the oxide produced;

the reduction of $Fe_2O_3$ with hydrogen or carbon oxide.

$$3Fe_2O_3+H_2 \rightarrow 2Fe_3O_4+H_2O$$

$$3Fe_2O_3+CO \rightarrow 2Fe_3O_4+CO_2$$

In a preferred embodiment, the metal oxide is one of the above listed iron oxides, namely FeO, $Fe_2O_3$, $Fe_3O_4$ or mixtures thereof. Most preferably iron(II) oxide.

Alternatively to an iron oxide, a copper oxide may be used. Copper oxide as meant herein refers to copper oxide (I), also known as cuprous oxide or $Cu_2O$, and to copper (II) oxide, also known as cupric oxide or CuO.

Another suitable metal oxide for use in the invention is aluminum oxide. Aluminum oxide is an oxide of aluminum with chemical formula $Al_2O_3$.

The temperature range in which the reaction is carried out is from 70° C. to 180° C., preferably from 85° C. to 170° C., particularly preferably from 90° C. to 160° C. When the reaction is performed at temperatures above 100° C., this must be carried out under pressure because of the vapor pressure. The overpressure is at least equal to the vapor pressure of the reaction mixture. The hydrolysis reaction is preferably carried out at a pressure in the range of 1 to 10 bar; more preferably between 2 and 8 bar, most preferably below 5 bar. The duration of the hydrolysis may range from 0.3 hours to 35 hours.

Figure 1:
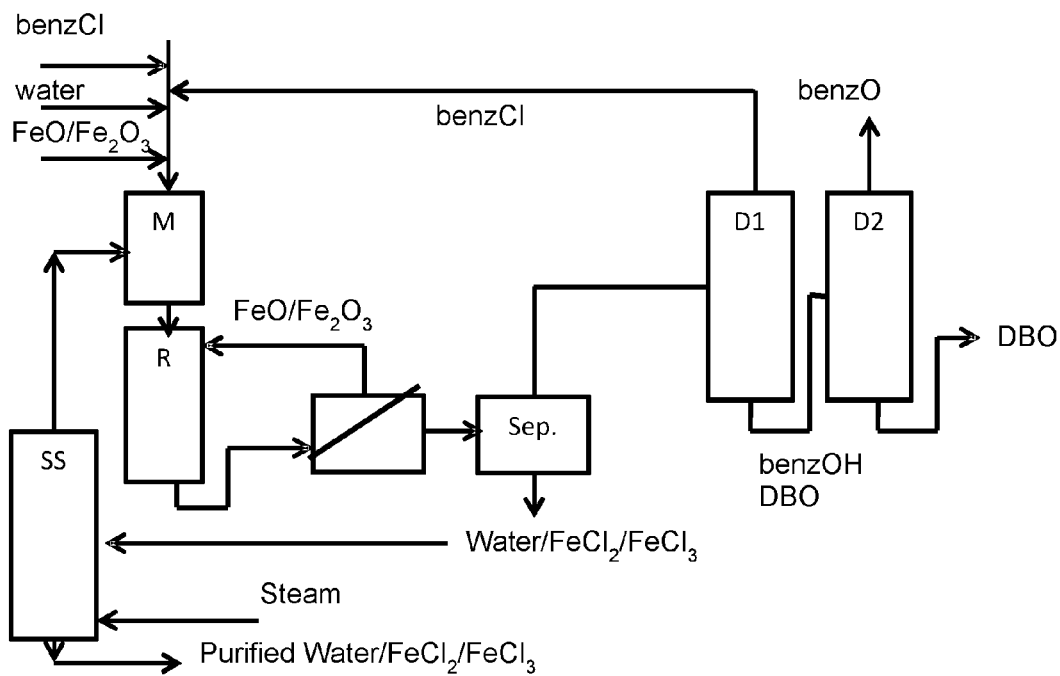
FIG. 1 depicts a schematic drawing of a set-up for a continuous hydrolysis of alpha-chlorinated toluenes, such as benzyl chloride.

The hydrolysis reaction can be carried out batch wise or continuously. The hydrolysis reaction according to the invention can be carried out in different types of reactors, for example a batch reactor or a continuously stirred tank reactor or combinations of different reactors. An example of a configuration suitable for continuous production of benzyl alcohol is depicted in FIG. 1.

Benzyl chloride (benzCl), water and a mixture of iron(II) oxide with iron(III)oxide ($FeO/Fe_2O_3$) are fed to a mixing tank M. Intensive mixing of these reagents is carried out. The intensive mixing of the reagents can be carried out by various methods known to the person skilled in the art, e.g. stirring, pumps, jets, baffles, turbulent flow in narrow tubes and by ultrasound. The mixture is fed to a reactor R where desired temperatures and pressure conditions are applied. From the bottom of the reactor a reaction mixture is lead to a separator, indicated in the Figure as a rectangle with a line from the lower left corner to the upper right corner. In the separator the remaining oxides are separated from the reaction mixture and returned to the reactor R. The remainder of the reaction mixture in the separator, after removal of at least part of the metal oxides, is fed to a second separator, denominated Sep. The aqueous solution of the metal chlorides is separated from the organic layer in the second separator (phase separator). The crude organic reaction mixture is fed to a first distillation column D1. From the first distillation column D1 non reacted benzyl chloride is removed overtop. It is returned to the conduit providing reactants to the mixing tank M. The bottom mixture of the first distillation column, mainly consisting of benzyl alcohol and dibenzyl oxide (DBO) is fed to a second distillation column D2. Here, the benzyl alcohol (benzOH) is distilled overtop and separated from dibenzyl oxide (DBO). The aqueous solution of metal chlorides is sent to a steam stripper SS to remove the organics, mainly benzylalcohol, overtop. The bottom outlet of the stripping column SS is an organic free solution of metal chlorides.

The inventors found that the use of metal oxides as hydrolyzing agents serves a double goal. First of all, the resulting aqueous liquors contain metal chlorides. These can easily be separated from the organic layer. They can be processed downstream as a valuable side stream since aqueous metal chlorides, particularly iron(III)chloride, are of commercial interest.

For example, iron(III)chloride is commercially available as a 40 wt % aqueous solution for use as flocculating and precipitating agent for the treatment of waste water and drinking water. Upon addition of small quantities of iron(III)chloride to the raw water to be treated, iron(III)hydroxide is formed. It precipitates and adsorbs finely divided solids and colloids. Removal from the iron(III)hydroxide from the water then provides treated water. Iron(III)chloride is also used in the chemical industry and in the electronic and printing industries.

Aqueous $FeCl_2$ resulting from the above described hydrolysis reaction, can be converted to the more sought after aqueous $FeCl_3$, by direct chlorination with chlorine or by oxy-chlorination with hydrochloric acid. In case higher iron content is desired, scrap iron and hydrochloric acid can be added to the aqueous $FeCl_2$ liquor. The scrap iron will be oxidized to $FeCl_2$ while the $FeCl_3$ (if present) is concomitantly reduced to $FeCl_2$. A number of reactions such as the formation of hydrogen may occur. The optimization of these reactions is within the knowledge of a person skilled in the art.

Secondly, the addition of the metal oxide lowered the concentration of hydrochloric acid in the reaction mixture during the conversion of the alpha-chlorinated toluene compounds. As the concentration of hydrogen chloride (HCl) in the aqueous solution could thereby be suppressed, an increase in HCl concentration could be controlled and the formation of byproducts was lowered.

Unexpectedly, not only did the byproduct formation decrease by using a metal oxide as hydrolyzing agent, also the conversion of the alpha-chlorinated toluene compound increased and more of the desired hydrolysis product resulted. This observation was in no way to be expected according to the state of the art.

The metal oxide is preferably used in an amount providing a molar ratio of metal oxide to alpha-chlorinated toluene compound of 0.5 to 1.5. More preferably the molar ratio of metal oxide to alpha-chlorinated toluene compound is between 0.5 to 1.0; most preferably between 0.5 to 0.8.

The alpha-chlorinated toluene compound is preferably used in an amount providing a molar ratio of alpha-chlorinated toluene compound to water of 1/10 to 1/50. More preferably the molar ratio of alpha-chlorinated toluene compound to water is between 1/15 and 1/40; most preferably between −1/20 and 1/35.

Preferably the above described hydrolysis reaction is used for the production of benzyl alcohol. A method according to an embodiment of the invention provides access to benzyl alcohol in an economically feasible way.

Metal chloride which is formed in a method according to an embodiment of the invention is preferably separated from the hydrolyzed compound. The removal of the metal chloride from the reaction mixture provides a product which can be valorized further, making the economics of the process even more attractive.

Separation processes for separating an aqueous solution of metal chloride from the reaction mixture are available to a person skilled in the art.

The metal chloride is separated from the reaction mixture in the form of an aqueous solution. Even more preferably the aqueous solution obtained is ready-for-use in another industrial process, e.g. in water treatment. For this purpose, the metal oxide used is preferably an iron oxide. Preferably the metal chloride is available as an aqueous metal chloride solution in a concentration of at least 20, preferably at least 30, most preferably at least 40 weight %. These concentrations are suitable for direct use in downstream application. Aqueous $FeCl_3$ can be used in water treatment application as coagulant.

The aqueous iron chloride can be stored in storage tanks without the need for further treatment. If required, it can first be send to an intermediate storage tank, brought to a desired concentration by the addition of more metal equivalents. To a product stream with $FeCl_2$, chlorination or oxy-chlorination may be applied to provide $FeCl_3$ or to increase the concentration of $FeCl_3$.

A method according to an embodiment of the invention has the advantage over prior art methods that it does not require the addition of a organic solvent for the extraction of the hydrolyzed compound, in particular benzyl alcohol, from the aqueous layer. The use of a metal oxide which is transformed in a metal chloride provides for easy separation of the organic layer from the aqueous layer. Standard, low pressure, equipment may be used. No bases or other additives are required.

In a preferred embodiment, the method is characterized by a conversion of alpha-chlorinated toluene compound of at least 85%, preferably at least 90%, most preferably at least 95%. The term conversion as used herein is presented by the following formula: the conversion of a substrate expressed in percent is the amounts of mole of substrate consumed divided by the amount of mol of substrate charged multiplied by hundred.

The term yield as used herein is presented by the following formula: the yield of a product expressed in percent is the amount of mol of a substrate consumed for the formation of product divided by the amount mol of substrate consumed multiplied by hundred.

The invention is further described by the following non-limiting examples which further illustrate the invention, and are not intended to, nor should they be interpreted to, limit the scope of the invention.

EXAMPLES

Example 1

Example 1, with reference to FIG. 2, illustrates the conversion of benzyl chloride to benzyl alcohol under ambient pressure and a temperature of 100° C. 11.2 g (0.089 mol) of benzyl chloride, 33.6 g (1.87 mol) of water and 3.18 g of FeO (0.044 mol) were heated to 100° C. under reflux with vigorous stirring (750 rpm). During the course of the conversion, the organic layer was analyzed by gas chromatography. A batch conversion of 96.5% benzyl chloride was found with a yield of 95% benzyl alcohol after 30.3 h of refluxing. This example supports the claim that the conversion of benzyl chloride to benzyl alcohol proceeded further in the presence of a metal oxide (in this particular case FeO) as hydrolyzing agent, compared to the same reaction in the absence of a metal oxide. In addition, formation of the byproduct dibenzyl oxide was lower.

Example 2

In the experiment of Example 2 benzyl chloride was hydrolyzed to benzyl alcohol at a temperature of 110° C. The hydrolysis was conducted in a Büchi miniclave with a working volume of 45 ml. 3.18 g of iron(II)oxide was added to 11.2 g benzyl chloride. Samples were taken of the reaction mixture at different time intervals. The results are summarized in Table 2. From Table 1 it can be seen that the concentration of the byproduct dibenzyl oxide rises significantly in function of time. The conversion rate at 110° C. was lower compared to the reaction executed at 125° C.

TABLE 1 conversion of benzyl chloride to benzyl alcohol using FeO and a reaction temperature of 110° C.

| benzCl/water (wt) | time (min) | benzCl | benzOH | DBO |
|---|---|---|---|---|
| 1/3 | 30 | 61.3 | 36.1 | 2.6 |
| 1/3 | 70 | 39 | 58.3 | 2.8 |
| 1/3 | 180 | 3.5 | 79.5 | 17 |

Example 3

In the experiment of Example 3 benzyl chloride was hydrolyzed to benzyl alcohol at a temperature of 150° C., using 3.18 g FeO for 11.2 g benzyl chloride. A weight ratio of benzyl chloride to water of 1 to 3 was used. The results obtained after a reaction time of 10 minutes are depicted in Table 2. The concentration of the byproduct dibenzyl oxide rises very quickly.

TABLE 2 conversion of benzyl chloride to benzyl alcohol using FeO and a reaction temperature of 150° C.

| benzCl/water (wt) | FeO (g) | time | benzCl | benzOH | DBO |
|---|---|---|---|---|---|
| 1/3 | 3.18 | 10 | 7.1 | 53.9 | 39 |

Example 4

In the experiment of Example 4 a lower than stoichiometric amount of hydrolyzing agent in this case FeO, was used. 11.2 g (0.089 mol) of benzyl chloride, 33.6 g (1.87 mol) of water and 2.22 g of FeO (0.031 mol) were heated to 125° C. in an autoclave with vigorous stirring (500 rpm, with stirring during heating period). After 10 minutes at 125° C., the liquid was cooled and the organic phase was separated and analyzed by gas chromatography. A conversion of 85% was found with a yield of 89.8% benzyl alcohol.

Example 5

In the experiment of Example 5, 11.2 g (0.089 mol) of benzyl chloride, 56 g (3.1 mol) of water and 3.18 g of FeO (0.044 mol) were heated to 125° C. in an autoclave with vigorous stirring (500 rpm, with stirring during heating period). After 10 minutes at 125° C., a conversion of 91% was found with a yield of 93%. The results of Example 5 illustrate the influence of a decreasing ratio of reactant to water: 3.1 mol of water versus 1.87 mol of water.

Example 6

In the experiment of Example 6, benzyl chloride is hydrolyzed to benzyl alcohol with one equivalent of Fe2O3. The weight ratio of water to benzyl chloride was 1/3. The reaction temperature was 100° C. The hydrolysis took place under atmospheric conditions and reflux, obtained by setting a cooler at a temperature of 10° C. The mixture was homogenized using a stirrer that rotated at 750 rpm. The results are depicted in FIG. 3. From the results it can be seen that a better conversion was obtained when using $Fe_2O_3$ as metal oxide compared to performing the hydrolysis without metal oxide.

Example 7

In the experiment of Example 7, copper oxide (CuO) is used as hydrolyzing agent to hydrolyze benzyl chloride to benzyl alcohol. 11.2 g (0.089 mol) of benzyl chloride, 33.6 g (3.1 mol) of water and 4.32 g of CuO (0.044 mol) were heated to 125° C. in an autoclave with vigorous stirring (500 rpm, with stirring during heating period). After 10 minutes heating time, a conversion of 90% was found with a yield of 93%.

What is claimed is:

1. A method for hydrolyzing alpha-chlorinated toluene compounds comprising the steps of:
   providing an alpha-chlorinated toluene compound of formula (I):

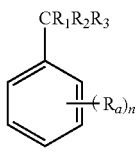

wherein a single group of $R_1$, $R_2$ and $R_3$ is Cl and the remaining R1, R2, and R3 groups are hydrogen, and wherein $(R_a)_n$ designates that the benzene nucleus may have one or more substituents which may be same or different and are selected from the group consisting of H, Cl, Br and $—C_mH_{2m+1}$, n being 0 or an integer from 1 to 5, and m being an integer, preferably from 1 to 6,
   hydrolyzing said compound with water in the presence of a metal oxide, wherein the molar ratio of metal oxide to alpha-chlorinated toluene compound is from 0.5 to 1.5;
   wherein the hydrolysis is carried out at a temperature in the range of 70° C. to 180° C., with the proviso that above 100° C. the reaction is carried out under pressure which pressure is at least equal to the vapor pressure of the reaction mixture; and wherein the molar ratio of alpha-chlorinated toluene compounds to water is from 1/10 to 1/50, thereby providing hydrolyzed alpha-chlorinated toluene compound.

2. The method according to claim 1, wherein the metal oxide is selected from the group consisting of iron oxides, cupper oxides, aluminum oxides and mixtures thereof.

3. The method according to claim 1, wherein the metal oxide is FeO, $Fe_2O_3$, $Fe_3O_4$ or mixtures thereof.

4. The method according to claim 1, wherein the metal oxide is FeO.

5. The method according to claim 1, wherein the alpha-chlorinated toluene compound is benzyl chloride.

6. The method according to claim 1, wherein the hydrolysis is carried out at a pressure in the range of 1 to 10 bars.

7. The method according to claim 6, wherein the resulting product of hydrolysis is benzyl alcohol.

8. The method according to claim 7, wherein an aqueous metal chloride side stream is separated from the hydrolysed compound.

9. The method according to claim 8, wherein $FeCl_2$ in the separated metal chloride side stream is converted into $FeCl_3$; by adding chlorine gas to the side stream or by oxy-chlorinating the side stream with HCl.

10. The method according to claim 9, wherein the aqueous $FeCl_3$ is transferred to a storage unit for use in water treatment.

11. The method according to claim 1, without the addition of an organic solvent for the extraction of the hydrolyzed compound.

12. The method according to claim 1, with a conversion of alpha-chlorinated toluene compound of at least 85%.

* * * * *